United States Patent [19]

Holt et al.

[11] Patent Number: 5,237,065
[45] Date of Patent: Aug. 17, 1993

[54] STEROID 5-ALPHA-REDUCTASE INHIBITORS

[75] Inventors: Dennis A. Holt, Downingtown; Mark A. Levy, St. Davids; Brian W. Metcalf, Radnor, all of Pa.

[73] Assignee: SmithKline Beecham Corporation, Philadelphia, Pa.

[21] Appl. No.: 830,806

[22] Filed: Feb. 4, 1992

Related U.S. Application Data

[62] Division of Ser. No. 419,563, Oct. 10, 1989, Pat. No. 5,110,939, which is a division of Ser. No. 7,539, Jan. 28, 1987, Pat. No. 4,888,336.

[51] Int. Cl.$^5$ .......................... C07J 75/00; C07J 73/00
[52] U.S. Cl. ......................................... 546/15; 544/63; 544/96; 544/125; 544/361; 544/335; 544/224; 546/77
[58] Field of Search ................. 544/96, 125, 361, 335, 544/224, 63; 546/77, 15

[56] References Cited

U.S. PATENT DOCUMENTS

| | | | |
|---|---|---|---|
| 3,022,312 | 2/1960 | Wildi | 546/77 |
| 4,317,817 | 3/1982 | Blohm et al. | 552/516 |
| 4,361,578 | 11/1982 | Alig et al. | 549/331 |
| 4,377,584 | 3/1983 | Rasmusson et al. | 546/15 |

OTHER PUBLICATIONS

Blohm, Biochem. and Biophys. Research Commun. 95(1), 1980 pp. 273–280.
Baumgarth et al. Tetrahedron 31 pp. 3119–3130, 1975.
Brooks et al. Steroids 47(1) 1986 1–19.
Rasmusson, J. Med. Chem. 1986 29 2298–2315.
Hsia et al. J. Invest. Derm. 224–227, 1974.
Overnell et al. J. Chem. Soc. C. 1971 378–384.
Petrow et al. Steroids 38(2) 1982 2764–2782.
Imperato-McGinley J. Steroid Biochem. 11 637–645, 1979.
Robaire et al. J. Steroid Biochem. 1977 (8) 307–310.
Llang et al. J. Steroid Biochem. 19(1) 385–390, 1983.

Primary Examiner—Mukund J. Shah
Assistant Examiner—E. C. Ward
Attorney, Agent, or Firm—Wayne J. Dustman; Stephen Venetianer; Edward T. Lentz

[57] ABSTRACT

Invented are 4-aza-5-alpha-8(14)-17 substituted-androsten-3-ones having an 8(14), 7(8), or 16(17) double bond, optionally also having a 1(2) double bond, pharmaceutical compositions containing the compounds, and methods of using these compounds to inhibit steroid 5-alpha-reductase.

1 Claim, No Drawings

STEROID 5-ALPHA-REDUCTASE INHIBITORS

This is a division of application Ser. No. 07/419,563, now U.S. Pat. No. 5,110,939 filed Oct. 10, 1989 which is a division of application Ser. No. 07/007,539 filed Jan. 28, 1987, now U.S. Pat. No. 4,888,336.

FIELD OF THE INVENTION

The present invention relates to novel 17-substituted-4-aza-5-alpha-17β-androsten-3-ones having an 8(14), 7(8), or 16(17) double bond, optionally also having a 1(2) double bond, pharmaceutical compositions containing these compounds, and methods for using these compounds to inhibit mammalian steroid 5-alpha-reductase.

DESCRIPTION OF RELATED ART

The class of steroidal hormones known as androgens are responsible for the physical characteristics that differentiate males from females. Of the several organs that produce androgens, the testes produce these hormones in the greatest amounts. Centers in the brain exert primary control over the level of androgen production. Numerous physical manifestations and disease states result when ineffective production control results in excessive androgen hormone production. For example, acne vulgaris, seborrhea, female hirsutism, and benign prostatic hypertrophy are correlated with elevated androgen levels. Additionally, the incidence of male pattern baldness has been associated with high androgen levels.

Testosterone is the principal androgen secreted by the testes and is the primary androgenic steroid in the plasma of males. It now is known that 5-alpha-reduced androgens are the active hormones in some tissues such as the prostate and sebaceous gland. Circulating testosterone thus serves as a prohormone for dihydrotestosterone (DHT), its 5-alpha-reduced analogue in these tissues but not in others such as muscle and testis. Steroid 5-alpha-reductase is a NADPH-dependent enzyme that converts testosterone to DHT. The importance of this enzyme in male development was dramatically underscored by discovery of a genetic steroid 5-alpha-reductase deficiency in male pseudohermaphrodites. Imperato-McGinley, J., et al., (1979), *J. Steroid Biochem.* 11:637–648.

Recognition of the importance of elevated DHT levels in many disease states has stimulated many efforts to synthesize inhibitors of this enzyme. The structures of several known steroid 5-alpha-reductase inhibitors are shown in Table 1.

TABLE 1

5-alpha-Reductase Inhibitors

| | | | |
|---|---|---|---|
| (1) | COOH | $K_1 = 1.1 \times 10^{-6}M$ (Reversible) | Hsia and Voight 1973 |
| (2) | O | $1 \times 10^{-6}M$ (Irreversible) | Robaire, et al., 1977 |
| (3) | OH | $3.5 \times 10^{-8}M$ (Irreversible) | Blohm, et al., 1980 |

TABLE 1-continued
5-alpha-Reductase Inhibitors

| | | | |
|---|---|---|---|
| (4) | 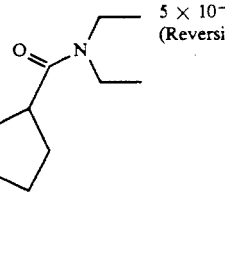 | $5 \times 10^{-9}$M (Reversible) | Liang, et al, 1983 |
| (5) | 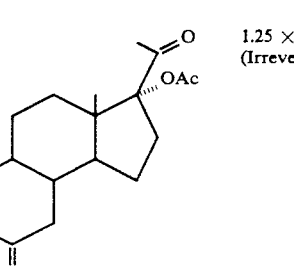 | $1.25 \times 10^{-6}$M (Irreversible) | Petrow, et al., 1981 |

The first inhibitor described was the 17-β-carboxylic acid (1) by Hsia and Voight in 1973. *J. Invest. Dermat.* 62:224–227. The secosteroid (2) was the next inhibitor to be described and also has found utility as an affinity label for 5-alpha-reductase. Robaire, B., et. al., (1977), *J. Steroid Biochem.* 8:307–310. The diazoketone (3) has been reported as a potent, time-dependent inhibitor of steroid 5-alpha-reductase. Blohm, T.R., et. al. (1980), *Biochem. Biophys. Res. Comm.* 95:273–280; U.S. Pat. No. 4,317,817, Mar. 2, 1982. Compound (4) is exemplary of a group of 4-aza steroid inhibitors of steroid 5-alpha-reductase described in U.S. Pat. No. 4,377,584 which issued Mar. 22, 1983, and in Liang, T., et al. (1983), *J. Steroid Biochem.* 19, 385–390. The 6-methylene steroid (5) also has been shown to be a time-dependent inactivator of steroid 5-alpha-reductase. Petrow, V., et. al. (1981), *Steroids* 38:121–140.

Other 5-alpha-reductase inhibitors also have been described. U.S. Pat. No. 4,361,578 which issued Jun. 2, 1986, describes a class of homosteroid enzyme inhibitors. Japanese Patents J60146855-A and J60116657-A disclose various aniline derivatives having numerous activities including 5-alpha-reductase inhibiting activity. Japanese Patent J60142941-A discloses phenyl-substituted ketones having 5-alpha-reductase inhibiting activity and European Patent EP173516-A discloses various phenyl-substituted amides having similar activity. Shiseido referenced terpene derivatives that are active inhibitors of steroid 5-al-oha-reductase. Japanese Patent No. J59053417-A.

SUMMARY OF THE INVENTION

The present invention resides in the discovery that steroid 5-alph-a-reductase is inhibited by 4-aza-5-alpha-17-substituted-androsten-3-one compounds having an 8(14), 7(8), or 16(17) double bond, optionally also having a 1(2) double bond. The compounds are potent enzyme inhibitors.

Presently preferred compounds of the invention and compounds used in the invented pharmaceutical compositions and the invented methods include:

4-methyl-4-aza-5-alpha-8(14)-pregnen-3-one-(20R)-20-carboxylic acid, (20R)-hydroxymethyl-4-methyl-4-aza-5-alpha-8(14)pregnen-3-one, and B 4-methyl-4-aza-5-alpha-8(14)-androsten-3-one-17β-N,N-diisopropylcarboxamide.

In a further aspect of the invention there are provided novel intermediates and novel processes useful in preparing the presently invented 5-alpha-reductase inhibiting compounds.

The invention also is a method for inhibiting 5-alpha-reductase activity in mammals, including humans, that comprises administering internally to a subject in need thereof an effective amount of a presently invented 5-alpha-reductase inhibiting compound.

Included in the present invention are pharmaceutical compositions comprising a pharmaceutical carrier and compounds useful in the methods of the invention.

DETAILED DESCRIPTION OF THE INVENTION

The presently invented compounds that inhibit 5-alpha-reductase have the following Formula (I):

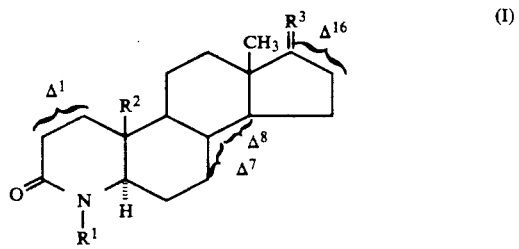

in which:

$\Delta^1$, $\Delta^7$, $\Delta^8$, and $\Delta^{16}$ are —CH$_2$—CH$_2$— or —CH=CH—, provided that one of $\Delta^7$, $\Delta^8$, and $\Delta^{16}$ is —CH=CH—;

R$_1$ is H or C$_{1-8}$ alkyl;

R$_2$ is H or C$_{1-8}$ alkyl;

R$_3$ is (1) alpha-hydrogen, alpha-hydroxyl, or acetoxy and (a)

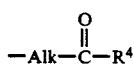

where Alk is absent or present as a straight or branched hydrocarbon chain of 1 to 12 carbons, and $R^4$ is
 (i) hydrogen,
 (ii) hydroxyl,
 (iii) $C_{1-8}$ alkyl,
 (iv) hydroxy $C_{1-8}$ alkyl,
 (v) $C_{1-8}$ alkoxl,
 (vi) $NR^5R^6$, where $R^5$ and $R^6$ are each independently selected from hydrogen, $C_{1-8}$ straight or branched chain alkyl, $C_{3-6}$ cycloalkyl, phenyl; or $R^5$ and $R^6$ taken together with the nitrogen to which they are attached represent a 5-6 membered saturated ring comprising up to one other heteroatom selected from oxygen and nitrogen, or
 (vii) $OR^7$, where $R^7$ is hydrogen, alkali metal, $C_{1-18}$ straight or branched chain alkyl, benzyl, or
  (b) —Alk—$OR^8$, where Alk is always present and has the same meaning as above, and is
  (i) phenyl $C_{1-6}$ alkylcarbonyl,
  (ii) $C_{5-10}$ cycloalkylcarbonyl,
  (iii) benzoyl,
  (iv) $C_{1-8}$ alkoxycarbonyl,
  (v) amino, or $C_{1-8}$ alkyl substituted amino, carbonyl, or
  (vi) hydrogen, provided that Alk is a branched $C_3$-$C_8$ chain,
(2) =CH—Alk—CO—$R^4$ or =CH—Alk—$OR^8$, where Alk is present or absent and has the same meaning as above, and $R^4$ and $R^8$ have the same meaning as above and $R^8$ also is hydrogen or $C_{1-20}$ alkylcarbonyl;
(3)

where the dashed bond replaces the 17-alpha-hydrogen,
(4) alpha-hydrogen and $NHCOR^9$ where $R^9$ is $C_{1-12}$ alkyl or $NR^5R^6$ where $R^5$ and $R^6$ have the same meaning as above,
(5) alpha-hydrogen and cyano,
(6) alpha-hydrogen and tetrazolyl, or
(7) keto;
or a pharmaceutically acceptable salt thereof.

As used herein $C_{1-n}$ alkyl means a straight or branched hydrocarbon chain having 1 to n carbons.

Preferred among the presently invented compounds are those having Formula (II):

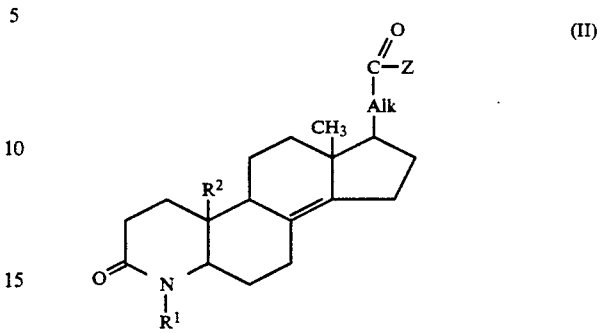

in which:

Z is H, alkyl, $C_{1-4}$ alkoxy, or $NR^{20}R^{21}$ wherein $R_{20}$ and $R^{21}$ independently are $C_{1-8}$ alkyl, Alk is absent or present as a straight or branched hydrocarbon chain of 1 to 4 carbons, and $R^1$ and $R^2$ are as defined in claim 1, or a pharmaceutically acceptable salt thereof.

Presently, the most preferred compounds of the invention are:

4-methyl-4-aza-5-alpha-8(14)-androsten-3-one-17β-N,N-diisopropylcarboxamide:

4-methyl-4-aza-5-alpha-8(14)-pregnen-3-one-(20R)-20-carboxylic acid; and (20R)-hydroxymethyl-4-methyl-4-aza-5-alpha-8(14)-pregnen-3-one.

Also preferred among the presently invented compounds are those having formula (X):

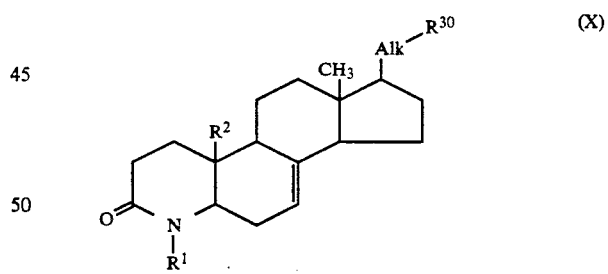

in which:

Alk is absent or present as a straight or branched hydrocarbon chain of 1 to 4 carbons, $R^{30}$ is hydroxy, halo, $C_{1-4}$ alkoxy, or $CO_2C_aH_{2a+1}$ wherein a is 1-5, and $R^1$ and $R^2$ are as described in Formula (I).

The compounds of Formula (I) wherein $\Delta^7$ or $\Delta^8$ is —CH=CH— are prepared according to either of the equally preferred synthetic pathways shown in Schemes I and II. In Schemes I and II, $R^1$, $R^2$, and $R^3$ are as defined in Formula (I) and $R^{20}$ is as defined in Formula (II).

Scheme I
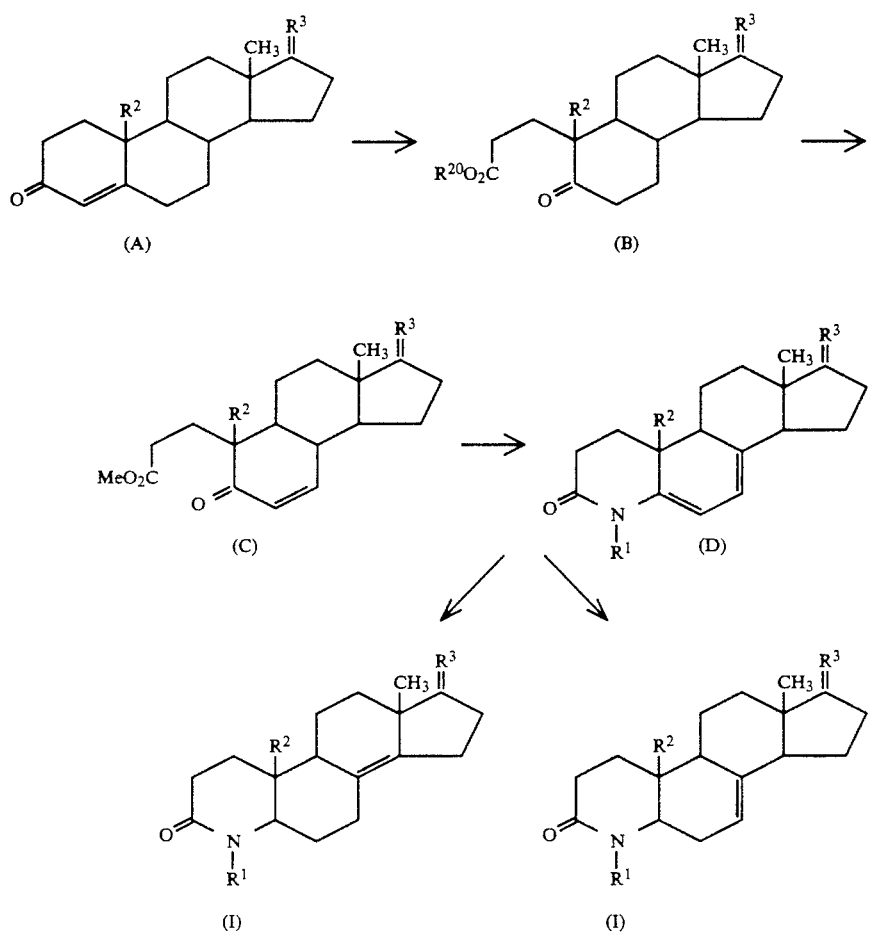
Scheme II
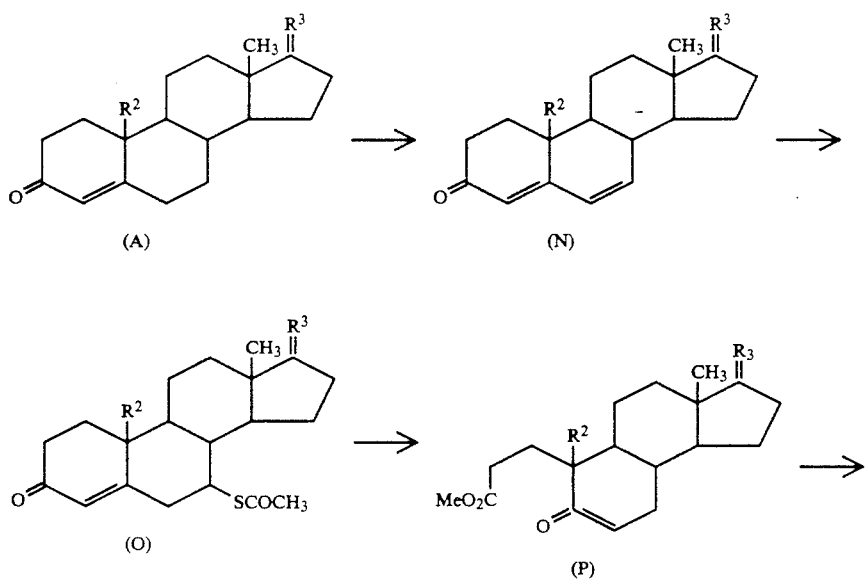

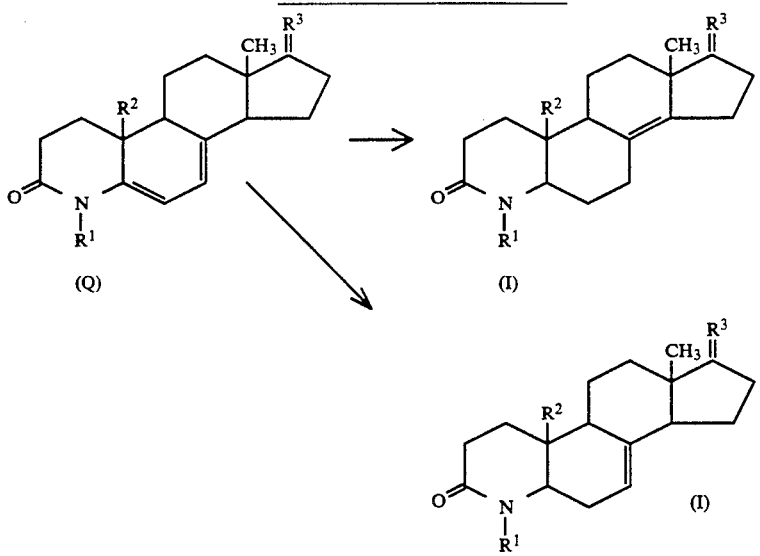

According to Scheme I, compound A is dissolved in a suitable organic solvent such as a $C_{1-4}$ alkyl dihalide in a $C_{1-4}$ alkanol, preferably methylene chloride in methanol, cooled to approximately $-100°$ C. to $30°$ C., preferably $-78°$ C. and treated with ruthenium dioxide/sodium periodate, potassium permanganate, or, preferably, an excess of ozone. The resulting solution is purged with an inert gas such as argon as it is warmed to approximately $25°$ C. to $50°$ C., preferably $40°$ C. The solution then is concentrated, the carboxylic acid (compound (B)) where $R^{20}$ is hydrogen is taken up in a suitable organic solvent such as dimethylacetamide, and in the presence of a base such as sodium bicarbonate or 1,8-diazabicyclo[5.4.0] undec-7-ene (DBU), reacted with a $C_{1-4}$ alkyl halide such as methylchloride, ethylchloride, methyl bromide or, preferably, methyl iodide to yield a formula (B) compound. Alternatively, the formula (B) compound is prepared by reaction of the carboxylic acid with diazomethane.

The keto-ester (B) in a suitable organic solvent such as ethyl acetate then is reacted with phenylselenyl chloride under inert gas such as argon. The resulting solution is cooled to approximately $0°$ C. to $30°$ C., preferably $15°$ C. and treated with an oxidizing agent such as ozone, meta-chloroperbenzoic acid, or, preferably, hydrogen peroxide while keeping the temperature below approximately $30°$ C. to yield a formula C compound.

Compounds of formula C then are combined with ammonia or a $C_{1-4}$ alkylamine selected to possess the desired $R^1$ substituent and heated to approximately $150°$ C. to $200°$ C., preferably $180°$ C. to prepare formula D compounds. Formula (I) compounds wherein $\Delta^8$ is —CH=CH— then are prepared by standard hydrogenation of formula D compounds using hydrogenation agents such as platinum dioxide, palladium on carbon, Raney nickel, preferably palladium on carbon and hydrogenation solvents such as suitable organic solvents. Formula (I) compounds wherein $\Delta^7$ is —CH=CH— are prepared by hydrogenation of formula (D) compounds using Raney nickel and close monitoring of the reaction to minimize or prevent formation of Formula (I) compounds wherein $\Delta^8$ is —CH=CH—.

Preparation of Formula (I) compounds according to Scheme II begins from the same starting materials as in Scheme I. Formula N compounds are prepared by reacting Formula A compounds with a quinone oxidant such as chloranil in a suitable organic solvent such as t-butanol. The Formula N compounds then are reacted with a nucleophilic thiol compound such as thiophenol, butylmercaptan, or preferably thiolacetic acid to produce formula O compounds.

The thioacetylenone of formula O then is dissolved in a suitable organic solvent such as a $C_{1-4}$ alkyldihalide in a $C_{1-4}$ alkanol, preferably methylene chloride in methanol, cooled to approximately $-100°$ C. to $0°$ C., preferably $-78°$ C., and treated with an excess of ozone. After purging with an inert gas such as argon, the solution is concentrated and treated with a strong base such as sodium hydroxide to produce a residue. The residue then is dissolved in a suitable organic solvent, cooled to approximately $-30°$ C. to $30°$ C., preferably $0°$ C. and, in the presence of a base such as sodium bicarbonate or DBU, treated with a $C_{1-4}$ alkyl halide such as methylchloride, ethylchloride, methyl iodide, or, preferably, diazomethane to yield a formula P compound.

Compounds of formula P then are combined with ammonia or a $C_{1-4}$ alkylamine selected to possess the desired $R^1$ substituent and heated to approximately $150°$ C. to $200°$ C., preferably $180°$ C. to yield formula Q compounds. Formula (I) compounds then are prepared by hyrogenation of formula P compounds using hydrogenation agents such as palladium on carbon, or Raney nickel, preferably platinum dioxide, and hydrogenation solvents such as suitable organic solvents. As in Scheme I, Formula (I) compounds wherein $\Delta^7$ is —CH=CH— are prepared by hydrogenation of formula Q compounds using Raney nickel and close monitoring of the reaction to minimize or prevent formation of Formula (I) compounds wherein $\Delta^8$ is —CH=CH—.

Formula (I) compounds wherein $\Delta^1$ is —CH=CH— are prepared from Formula (I) compounds synthesized according to Schemes I or II by known oxidation and elimination reactions as described, for example, in Example 7. Formula (I) compounds wherein $\Delta^{16}$ is —CH=CH— are prepared by known dehydrogenation reactions as described, for example, in Example 10, from 17-keto Formula I compounds synthesized according to Schemes I or II.

Compounds of formula A, the starting materials in Schemes I and II, are prepared from the analogous 17-keto compounds by known procedures such as described in 2 J. Fried and J. Edwards, *Organic Reactions in Steroid Chemistry*, Pub: Van Nostrand Reinhold Company (1972). The 17-keto compounds are available and can be synthesized by known procedures. The starting materials are selected so that the $R^2$ and $R^3$ groups in the formula A compound are the same as the $R^2$ and $R^3$ groups in the Formula (I) compound being synthesized. Alternatively, the $R^2$ and $R^3$ groups of the formula A compound are selected so that they can be converted by known procedures to the $R^2$ and $R^3$ groups of the target Formula I compound by additional steps in the synthetic process. For example, Formula (I) compounds wherein $R^3$ is carboxylic acid are converted to the corresponding amides by reaction with amines or substituted amines via the corresponding acid chlorides. Similarly, Formula (I) compounds wherein $R^3$ is $CH_3CHCOOH$ is prepared by oxidation of the corresponding alcohol.

Pharmaceutically acceptable acid addition salts of the compounds of the invention are formed where appropriate with strong or moderately strong organic or inorganic acids in the presence of a basic amine by methods known to the art. For example, the base is reacted with an inorganic or organic acid in an aqueous miscible solvent such as ethanol with isolation of the salt by removing the solvent or in an aqueous immiscible solvent when the acid is soluble therein, such as ethyl ether or chloroform, with the desired salt separating directly or isolated by removing the solvent. Exemplary of the acid addition salts which are included in this invention are maleate, fumarate, lactate, oxalate, methanesulfonate, ethanesulfonate, benzenesulfonate, tartrate, citrate, hydrochloride, hydrobromide, sulfate, phosphate and nitrate salts. Pharmaceutically acceptable base addition salts of compounds of the invention prepared by known methods include nontoxic alkali metal and alkaline earth salts, for example, calcium, sodium, and potassium salts; ammonium salts, and salts of nontoxic organic bases such as triethylamine, butylamine, piperazine, and (trihydroxymethyl)methylamine.

In preparing the presently invented compounds of Formula I, novel intermediates of the following Formula III and IV are synthesized.

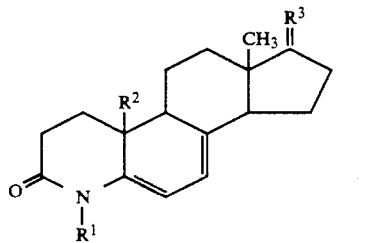

(III)

in which:
$R^1$ is H or $C_{1-8}$ alkyl;
$R_2$ is H or $C_{1-8}$ alkyl;
$R_3$ is
(1) alpha-hydrogen, alpha-hydroxyl, or acetoxy and
(a)

$$-Alk-\overset{O}{\underset{\|}{C}}-R^4$$

where Alk is absent or present as a straight or branched hydrocarbon chain of 1 to 12 carbons, and $R^4$ is
(i) hydrogen,
(ii) hydroxyl,
(iii) $C_{1-8}$ alkyl,
(iv) hydroxy $C_{1-8}$ alkyl,
(v) $C_{1-8}$ alkoxy,
(vi) $NR^5R^6$, where $R^5$ and $R^6$ are each independently selected from hydrogen, $C_{1-8}$ straight or branched chain alkyl, $C_{3-6}$ cycloalkyl, phenyl; or $R^5$ and $R^6$ taken together with the nitrogen to which they are attached represent a 5-6 membered saturated ring comprising up to one other heteroatom selected from oxygen and nitrogen, or
(vii) $OR^7$, where $R^7$ is hydrogen, alkali metal, $C_{1-18}$ straight or branched chain alkyl, benzyl, or (b) $-Alk-OR^8$, where Alk is always present and has the same meaning as above, and $R^8$ is
(i) phenyl $C_{1-6}$ alkylcarbonyl,
(ii) $C_{5-10}$ cycloalkylcarbonyl,
(iii) benzoyl,
(iv) $C_{1-8}$ alkoxycarbonyl,
(v) amino, or $C_{1-8}$ alkyl substituted amino, carbonyl, or
(vi) hydrogen, provided that Alk is a branched $C_3$-$C_8$ chain, (2) $=CH-Alk-CO-R^4$ or $=CH-Alk-OR^8$, where Alk is present or absent and has the same meaning as above, and $R^4$ and $R^8$ have the same meaning as above and $R^8$ also is hydrogen or $C_{1-20}$ alkylcarbonyl;

(3)

where the dashed bond replaces the 17-alpha hydrogen,
(4) alpha-hydrogen and $NHCOR^9$ where $R^9$ is $C_{1-12}$ alkyl or $NR^5R^6$ where $R^5$ and $R^6$ have the same meaning as above,
(5) alpha-hydrogen and cyano,
(6) alpha-hydrogen and tetrazolyl, or
(7) 17-keto.

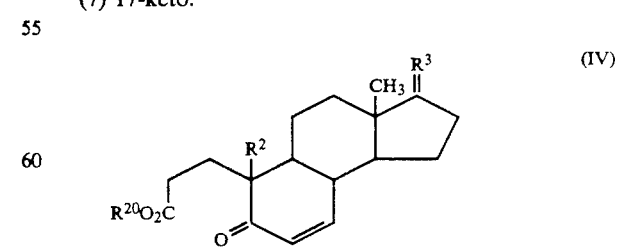

(IV)

in which:
$R_2$ is H or $C_{1-8}$ alkyl;
$R_3$ is
(1) alpha-hydrogen, alpha-hydroxyl, or acetoxy and (a)

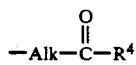

where Alk is absent or present as a straight or branched hydrocarbon chain of 1 to 12 carbons, and $R^4$ is
(i) hydrogen,
(ii) hydroxyl,
(iii) $C_{1-8}$ alkyl,
(iv) hydroxy $C_{1-8}$ alkyl,
(v) $C_{1-8}$ alkoxy,
(vi) $NR^5R^6$, where $R^5$ and $R^6$ are each independently selected from hydrogen, $C_{1-8}$ straight or branched chain alkyl, $C_{3-6}$ cycloalkyl, phenyl; or $R^5$ and $R^6$ taken together with the nitrogen to which they are attached represent a 5-6 membered saturated ring comprising up to one other heteroatom selected from oxygen and nitrogen, or
(vii) $OR^7$, where $R^7$ is hydrogen, alkali metal, $C_{1-18}$ straight or branched chain alkyl, benzyl, or
(b) —Alk—$OR^8$, where Alk is always present and has the same meaning as above, and $R^8$ is
(i) phenyl $C_{1-6}$ alkylcarbonyl,
(ii) $C_{5-10}$ cycloalkylcarbonyl,
(iii) benzoyl,
(iv) $C_{1-8}$ alkoxycarbonyl,
(v) amino, or $C_{1-8}$ alkyl substituted amino, carbonyl, or
(vi) hydrogen, provided that Alk is a branched $C_3$-$C_8$ chain,
(2) =CH—Alk—CO—$R^4$ or =CH—Alk—$OR^8$, where Alk is present or absent and has the same meaning as above, and $R^4$ and $R^8$ have the same meaning as above and $R^8$ also is hydrogen or $C_{1-20}$ alkylcarbonyl;
(3)

where the dashed bond replaces the 7-alpha hydrogen,
(4) alpha-hydrogen and $NHCOR^9$ where $R^9$ is $C_{1-12}$ alkyl or $NR^5R^6$ where $R^5$ and $R^6$ have the same meaning as above,
(5) alpha-hydrogen and cyano,
(6) alpha-hydrogen and tetrazolyl,
(7) 17-keto, and
$R^{20}$ is $C_{1-8}$ alkyl.

Because Formula (I) compounds inhibit steroid 5-alpha-reductase activity, they have therapeutic utility in treating diseases and conditions wherein decreases in DHT activity produce the desired therapeutic effect. Such diseases and conditions include acne vulgaris, seborrhea, female hirsutism, prostate diseases such as benign prostatic hypertrophy, and male pattern baldness. The potency of several compounds of the invention were tested for potency in inhibiting human steroid 5-alpha-reductase using tissue from hyperplastic human prostates. In determining potency in inhibiting the human enzyme, the following procedure was employed:

Frozen human prostates were thawed and minced into small pieces ($<5mm^3$). The tissue was homogenized in 3 to 5 volumes of 20 mM potassium phosphate, pH 6.5, buffer containing 0.33 M sucrose, 1 mM dithiothreitol, and 50 $\mu$M NADPH with a Brinkmann Polytron (Sybron Corporation, Westbury, N.Y.). The solution was subjected to sonication for 3 to 5 minutes with a Sonifier (Branson Sonic Power Co.) followed by hand homogenization in a glass-to-glass Dounce homogenizer (Kontes Glass Company, Vineland, N.J.).

Prostatic particles were obtained by differential centrifugation at 600 or 1000$\times$g for 20 minutes and 140,000$\times$g for 60 minutes at 4° C. The pellet obtained from the 140,000$\times$g centrifugation was washed with 5 to 10 tissue volumes of the buffer described above and recentrifuged at 140,000$\times$g. The resulting pellet was suspended in 20 mM potassium phosphate buffer, pH 6.5, containing 20% glycerol, 1 mM dithiothreitol, and 50 $\mu$M NADPH. The suspended particulate solution was stored at $-80°$ C.

A constant amount of [$^{14}$C]-testosterone (52 to 55 mCi/mmol, New England Nuclear, Boston, Mass.) in ethanol and varying amounts of the potential inhibitor in ethanol were deposited in test tubes and concentrated to dryness in a SAVANT Speed Vac. To each tube was added buffer, 20 $\mu$l of 10 mM NADPH and an aliquot of prostatic particulate solution to a final volume of 0.5 ml of 50 mM sodium citrate, pH 5.0. After incubating the solution at 37° C. for 20 to 30 minutes the reaction was quenched by the addition of 4 ml ethyl acetate and 0.25$\mu$ mol each of testosterone, dihydrotestosterone, androstanediol, and androstanedione as carriers. The organic layer was removed to a second test tube and evaporated to dryness in a Speed Vac. The residue was dissolved in 20 to 30 $\mu$l chloroform, spotted on an individual lane of a 20$\times$20 cm prechannelled silica gel TLC plate (Si 250F-PA, Baker Chemical) and developed twice with acetone:chloroform (1:9). The radiochemical content in the bands of the substrate and the products was determined with a BIOSCAN Imaging Scanner (Bioscan, Inc., Washington, D.C.). The percent of recovered radiolabel converted to product was calculated, from which enzyme activity was determined. All incubations were conducted such that no more than 12% of the substrate (testosterone) was consumed.

The experimentally obtained data was computer fitted to a linear function by plotting the reciprocal of the enzyme activity (1/velocity) against the variable inhibitor concentration (Dixon, M. (1953), *Biochem. J.*, 55, 170). Assuming that the steroidal inhibitor is a competitive inhibitor against testosterone, a value for the inhibition constant ($K_i$) can be calculated from equation 1:

$K_i = (B/A)/S/K + 1)$  Equation 1 where B is the intercept on the 1/velocity axis, A is the slope of the line, S is the concentration of substrate (testosterone) used in the experiment, and $K_m$ is the Michaelis-Menton constant of the substrate (testosterone) determined in a separate experiment to be 4.5 $\mu$M.

TABLE II

Inhibition Constants of Human Prostatic Steroid 5-alpha-Reductase

| Compound | | $K_i$ (nM) |
|---|---|---|
| (1) | 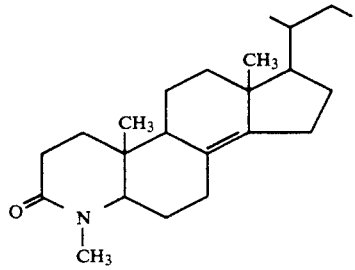 | 450 ± 20 |
| 2) | 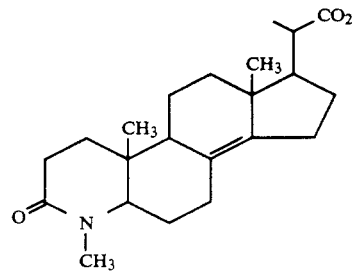 | 100 ± 10 |
| 3) | 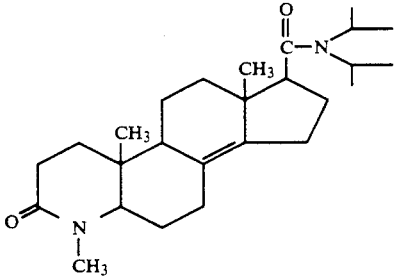 | 8 ± 2 |

Table II displays the results of the above testing and shows that the tested compounds of the invention are potent inhibitors of human steroid 5-alpha-reductase.

Certain compounds of the invention also were tested for their in vivo potency in inhibiting steroid 5-alpha-reductase activity. Male Charles River CD rats, 48 days old, weighing approximately 200 gm were administered the compounds of the invention shown in Table III dissolved in propylene glycol and diluted in normal saline. The compounds were administered orally at dosages of 5, 10, and 20 mg/kg. Six hours following compound administration the animals were sacrificed, the ventral prostates were excised, and testosterone (T) and DHT levels were measured by the following procedure.

Prostate tissue was excised, trimmed, weighed, minced and washed with phosphate buffer. The tissue then was homogenized in phosphate buffer and extracted by addition of ethyl acetate and mixing on an orbital mixer for forty-five minutes. The ethyl acetate was evaporated, the residue was reconstituted in ethanol, and was centrifuge filtered using 0.45 μM filter paper. The components then were separated using reverse-phase HPLC collecting T and DHT fractions. The fractions were reduced to dryness and reconstituted in standard T/DHT assay buffer available from Amersham. T and DHT levels then were measured using standard techniques such as radioimmunoassay.

[THIS SPACE INTENTIONALLY LEFT BLANK]

TABLE III

| Compound | | T* | DHT | T/DHT* |
|---|---|---|---|---|
| Control | | 0.67 ± .04 | 2.08 ± .16 | 0.32 |
| (20R)-Hydroxy-methyl-4-methyl-4-aza-5-alpha-8(14)-pregnen-3-one | 5 mg/kg | 0.52 ± .27 | 0.72 ± .21 | 0.72 |
| | 10 mg/kg | 0.44 ± .13 | 0.53 ± .12 | 0.83 |
| | 20 mg/kg | 0.45 ± .12 | 0.49 ± .14 | 0.92 |
| 4-Methyl-4-aza-5-alpha-8(14)-pregnen-3-one-(20R)-20-carboxylic acid | 5 mg/kg | 0.34 ± .11 | 0.43 ± .12 | 0.79 |
| | 10 mg/kg | 0.26 ± .07 | 0.34 ± .09 | 0.76 |
| | 20 mg/kg | 0.30 ± .04 | 0.34 ± .06 | 0.88 |

*T and DHT levels are given in ng/100 mg ventral prostate tissue ± SEM

In Table III the results obtained in the compound treated animals are compared to those obtained in vehicle-treated controls. As the data demonstrate, each of the dosage levels tested produced substantial decreases in prostatic DHT levels thus increasing T/DHT ratios. Therefore, the invented compounds are potent steroid 5-alpha-reductase inhibitors in vivo.

The time course of in vivo 5-alpha-reductase inhibition produced by compounds of the invention also was examined. Using procedures similar to those used in generating the data displayed in Table III, rats were administered 4-methyl-4-aza-8(14)-androsten-3-one-17β-N,N-diisopropylcarboxamide and ventral prostate tissue was excised for T and DHT determinations at several post-administration time points. As the data in Table IV demonstrate, when compared to controls, significant differences in DHT levels were observed at 1, 2, 4, and 8 hours following compound administration.

TABLE IV

| | Control | 1 Hour | 2 Hours | 4 Hours | 8 Hours |
|---|---|---|---|---|---|
| T (ng/100 mg tissue)* | .436 ± .12 | .533 ± .15 | .481 ± .12 | .607 ± .24 | .565 ± .16 |
| DHT (ng/100 mg tissue)* | .754 ± .10 | .532 ± .08** | .496 ± .05** | .504 ± .09** | .498 ± .04** |
| T/DHT | .58 | 1.00 | .97 | 1.20 | 1.13 |

*Data shown as mean ± SEM
**$P < .05$

The compounds of Formula I are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, Preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the present compounds of Formula I in a pharmaceutical dosage unit as described above will be an efficacious, nontoxic quantity selected from the range of 0.1–1000 mg/kg of active compound, preferably 1–100 mg/kg. The selected dose is administered to a human patient in need of steroid 5-alpha-reductase inhibition from 1–6 times daily, orally, rectally, by injection, or continuously by infusion. Oral dosage units for human administration preferably contain from 1 to 500 mg of active compound. Parenteral administration, which uses lower dosages is preferred. Oral administration, at higher dosages, however, also can be used when safe and convenient for the patient.

The method of this invention of inhibiting steroid 5-alpha-reductase activity in mammals, including humans, comprises administering internally to a subject in need of such inhibition an effective steroid 5-alpha-reductase inhibiting amount of a compound of Formula I.

Contemplated equivalents of Formula I compounds are compounds otherwise corresponding thereto wherein substituents have been added to any of the unsubstituted positions of the Formula I compounds or the methyl group at C-13 is absent or replaced by $C_{1-4}$ alkyl provided such compounds have the pharmaceutical utility of Formula (I) compounds.

The following examples illustrate preparation of Formula I compounds and pharmaceutical compositions containing these compounds. The examples are not intended to limit the scope of the invention as defined hereinabove and as claimed below.

EXAMPLE 1

(20R)-Hydroxymethyl-4-methyl-4-aza-5-alpha-8(14)-pregnen-3-one (i) (20R)-20-Hydroxymethyl-4-pregnen-3-one To a solution of (20R)-3-oxopregn-4-ene-20carboxaldehyde (100 g, 305 mmol, commercially available from Upjohn) in 1500 ml ethanol and 250 ml tetrahydrofuran cooled to approximately 5° C. was added sodium borohydride (3.35 g, 89 mmol) portionwise to keep the temperature below 15° C. After 20 minutes, acetic acid (100 ml) was added and the mixture was concentrated to a slush on a rotary evaporator. The residue was then taken up in chloroform, successively washed with water and brine, then dried over sodium carbonate and concentrated to yield (20R)-20-hydroxymethyl-4-pregnen-3-one as a white solid (100 g, 100%).

(ii) Methyl (20R)-20-hydroxymethyl-5-oxo-3,5-secopregnan-3-oate

The above enone (100 g, 303 mmol) was dissolved in 1000 ml dichloromethane and 500 ml methanol, cooled to −78° C., and treated with an excess of ozone. The resulting solution was purged with argon as it was warmed to 40° C. The solution was then concentrated to a viscous colorless oil, taken up in 500 ml dimethylacetamide, and stirred in the dark under argon with 50 g sodium bicarbonate and 50 ml methyl iodide for 48 hours. The reaction mixture was then poured into 4 μl of cold brine and extracted with dichloromethane. The organic extracts were thoroughly washed with water and brine then dried over sodium sulfate and concentrated to a yellow-red oil. This oil was filtered through 1000 g of silica gel with 25% ethyl acetate in hexane to yield, after concentration, the keto ester xethyl (20R)-20-hydroxymethyl-5-oxo3,5-secopregnan-3-oate as a lightly yellow viscous oil (71.8 g, 65%).

(iii) Methyl (20R)-20-hydroxymethyl-5-oxo-3,5-seco-6-pregnen-3-oate

To the keto-ester from above (71.8 g, 197 mmol) in 1500 ml ethyl acetate was added phenylselenyl chloride (45 g, 235 mmol) and the resulting dark solution was stirred under argon for three hours. The solution was then washed with water, saturated sodium bicarbonate, water, brine, and dried over potassium carbonate. The ethyl acetate solution was then cooled to 15° C. and treated with 30% hydrogen peroxide (65 ml) keeping the temperature below 30° C. After 1.5 hours, the solution was washed with water, saturated sodium carbonate, water, brine, dried and concentrated to a yellow foam (65 g). Column chromatography (silica, 25% ethyl acetate in hexane) yielded the ester-enone methyl (20R)-20-hydroxymethyl-5-oxo-3,5-seco-6-pregnen-3-oate as a colorless viscous oil (3 g, 32%).

(iv) (20R)-Hydroxymethyl-4-methyl-4-aza-5,7-pregnadien3-one

To the viscous ester-enone from above (1.67 g, 4.6 mmol) was added 10 ml ethylene glycol. Methylamine (3.5 g) was then bubbled into the glycol during which time the ester-enone dissolved. The solution was slowly heated to 180° C. for 20 minutes before cooling to ambient temperature. The resulting dark solution was diluted with cold water and thoroughly extracted with chloroform. The combined extracts were washed with water, brine, dried and concentrated to a brown foam (1.74 g) which was chromatographed (silica, 20% ethyl acetate in hexane) to yield dienamide (20R)-hydroxymethyl-4-methyl-4-aza-5,7-pregnadien-3-one as a white solid (380 mg, 24%).

(v) (20R)-Hydroxymethyl-4-methyl-4-aza-5-alpha-8(14)pregnen-3-one

The dienamide from above (500 mg, 1.38 mmol) in 100 ml ethyl acetate containing 1% ethanol was hydrogenated at 25° C. and 1 atm over 1.3 g 10% Pd on carbon for 3 hours. The solution was filtered to remove catalyst and concentrated to a white solid. Recrystallization from ethyl acetate afforded 300 mg (20R)-hydroxymethyl-4-methyl-4-aza -5-alpha-8(14)-pregnen-3-one as a white crystalline solid, m.p. (uncorrected) 219°–220° C.

EXAMPLE 2

4-Methyl-4-aza-5-alpha-8(14)-pregnen-3-one20R)-20-carboxylic acid

To a solution (20R)-hydroxymethyl-4-methyl-4-aza5-alpha-8(14)-pregnen-3-one (200 mg, 0.56 mmol), prepared in Example 1, in 15 ml acetone and 1 ml tetrahydrofuran was added Jones reagent dropwise until a red color persisted. Isopropanol was then added to quench the excess oxidant. The solution was decanted from the gummy chromium salts, concentrated, and partioned between dichloromethane and water. The salts were dissolved in water and extracted with dichloromethane. The combined organic layers were then washed with brine, dried over sodium sulfate, and concentrated to a white solid. Recrystallization from methanol/ethyl acetate afforded as white crystals 4-methyl-4-aza-5-alpha-8(14)-pregnen-3-one-(20R)-20-carboxylic acid (157 mg) (112 mg, 54%), m.p. (uncorrected) 310°–315° C.

EXAMPLE 3

4-Methyl-4-aza-5-alpha-8(14)-androsten-3-one-17βN,N,-diisopropylcarboxamide (i) Methyl androst-4,6-diene-3-one-17β-carboxylate Methyl androst-4-ene-3-one-17β-carboxylate (10 g, 30.3 mmol, prepared according to Rasmusson, et al., *J. Med. Chem.* 27 1960 (1984)) and chloranil (8.95 g, 36.4 mmol) in 700 ml t-butanol was heated at reflux for 3.5 hours then cooled and filtered. The filtrate was concentrated and the residue taken up in 700 ml chloroform and washed successively with 4×150 ml water, 3×150 ml saturated sodium bicarbonate, 3×150 ml 5% sodium hydroxide, 3×150 ml brine, dried over sodium sulfate, and concentrated to yield methyl androst-4,6-diene-3one-17β-carboxylate as a dark foam (7.0 g, 70%).

(ii) Methyl-6-thioacetyl-androst-4-ene-3-one-17β-carbonate

The dienone from above (7.0 g, 21.3 mmol) and thioacetic acid (15 ml) were heated at reflux for 2.5 hours. Excess thioacetic acid was then removed in vacuo and the residue was dissolved in 100 ml ethyl acetate and washed with water, saturated sodium bicarbonate, brine, dried and concentrated to yield methyl 6-thioacetylandrost-4-ene-3-one-17β-carboxylate as a dark oil (8.46 g, 98%).

(iii) Dimethyl 3,5-seco-6-androsten-5-one-3-17β-dicarboxylate

The thioacetyl-enone from above (17.0 g, 42.1 mmol) in 100 ml dichloromethane and 50 ml methanol at −78° C. was treated with excess ozone. The resulting solution was purged with argon, warmed to ambient temperature, and concentrated. The residue was dissolved in 100 ml methanol and 20 ml 10% sodium hydroxide and heated at reflux for 3 hours. The solution was then acidified with hydrochloric acid, concentrated, and partitioned between chloroform and water. The aqueous layer was further extracted with chloroform and the combined organic layers were washed with brine, dried, and concentrated. The residue was taken up in diethyl ether with enough dichloromethane to effect dissolution, cooled to 0° C. and treated with an ethereal solution of excess diazomethane. Concentration of the resulting solution afforded 10.5 g of a yellow oil which was chromatographed (silica, 30% ethyl acetate in hexane) to afford compound dimethyl 3,5-seco-6-androsten-5-one-3-17β-dicarboxylate (5.0 g, 33%) as a colorless oil.

(iv) Hydroxyethyl 4-methyl-4-aza-5,7-androstadien3-one-17β-carboxylate

To the enone-ester from above (5.0 g, 13.8 mmol) and 50 ml ethylene glycol was added methylamine (10 g) after which the enone-ester was dissolved. The resulting solution was then heated over a 90 minute period to 180° C. and held at that temperature for 20 minutes before cooling to ambient temperature. The resulting dark solution was diluted with cold water and thoroughly extracted with chloroform. The combined organic extracts were then washed with water and brine, dried, and concentrated to a dark brown oil. Chromatography (silica, 1:1 ethyl acetate/hexane) afforded dienamide hydroxyethyl 4-methyl-4-aza-5,7-androstadien-3-one-17β-carboxylate (1.5 g, 29%) as an off-white solid.

(v) Hydroxyethyl 4-methyl-4-aza-8(14)-androsten-3-one17β-carboxylate

The dienamide from above (1.5 g, 4.02 mmol) in 20 ml 10% ethanol in ethyl acetate was hydrogenated over 1.5 g palladium dioxide at ambient temperature and 1 atm. for 3 hours. The catalyst was then removed by filtration and the solution was concentrated to yield hydroxyethyl 4-methyl-4-aza-8(14)-androsten-3-one-17βcarboxylate as a white solid (1.5 g).

(vi) 4-Methyl-4-aza-8(14)-androsten-3-one-17β-carboxylic acid

The hydroxyethyl ester from above (1.5 g, 4.0 mmol) and potassium carbonate (3 g) in 150 ml 10:1 xethanol-water was heated at reflux for 12 hours. The resulting mixture was concentrated, diluted with water, acidified, and thoroughly extracted with chloroform. The chloroform was evaporated and the residue was chromatographed (silica, 5% methanol in dichloromethane) to yield 4-methyl-4-aza-8(14)-androsten-3-one-17β-carboxylic acid (0.75 g, 57%) as a white solid.

(vii) 4-Methyl-4-aza-8(14)-androsten-3-one-17β-carboxylic acid chloride

A solution of the acid from above (250 mg, 0.75 mmol) in toluene (8 ml) was treated with 0.5 ml oxalyl chloride. After 2 hours the volatile materials were removed at 1 mmHg leaving a residue of 4-methyl-4-aza-8(14)-androsten-3-one-carboxylic acid chloride.

(viii) 4-Methyl-4-aza-5-alpha-8(14)-androsten-3-one17β-N,N-diisopropylcarboxamide A solution of the above acid chloride (283 mg, 0.75 mmol) in 8 ml tetrahydrofuran was treated with 1 ml diisopropylamine overnight. The solution was diluted with water and extracted thoroughly with dichloromethane. The extracts were dried and concentrated to a white solid. Preparative HPLC (silica, 10% isopropyl alcohol in hexane) followed by recrystallization from diethyl ether afforded 4-methyl-4-aza-5-alpha-8(14)-androsten -3-one-17β-N,N-diisopropylcarboxamide (100 mg), m.p. (uncorrected) 185°–190° C.

EXAMPLE 4

4-Methyl-4-aza-8(14)-androsten-3-one-17β-carboxaldehyde

A solution of 4-methyl-4-aza-8(14)-androsten-3-one-17β-carboxylchlic acid chloride (378 mg, 1 mmol), prepared as in Example 3, in 10 ml tetrahydrofuran is treated with lithium tri-t-butoxyaluminum hydride (254 mg, 1 mmol) at 0° C. for one hour to yield, after aqueous workup, 4-methyl-4-aza-8(14)-androsten-3-one-17β-carboxaldehyde.

EXAMPLE 5

4-Methyl-4-aza-17β-(1-oxobutyl)-8(14)-androstene-3-one

A solution of 4-methyl-4-aza-8(14)-androsten-3-one-17β-carboxylic acid chloride (378 mg, 1 mmol) in 10 ml tetrahydrofuran is treated with di-n-butyl copperlithium −78° C. The reaction is quenched with aqueous ammonium chloride. Extraction with dichloromethane followed by concentration of the organic extract yields 4-methyl-4-aza-17β-(1-oxobutyl)-8(14)-androstene-3-one.

EXAMPLE 6

(20R)-Hydroxymethyl-4-methyl-4-aza-5-alpha-7-pregnen-3-one

Active Raney nickel W-2 catalyst (500 mg) which had been washed with water, ethanol, and ethyl acetate, was suspended in a solution of (20R-hydroxymethyl-4-methyl4-aza-5,7-pregnadien-3-one (115 mg, 0.33 mmol), prepared as in Example 1, in 15 ml ethyl acetate and stirred under 1 atm. of hydrogen for twenty hours. The catalyst was then removed by filtration and the filtrate was concentrated to a white solid. Chromatography (silica, 6:3:1 cyclohexane-acetone-ethyl acetate) afforded 56 mg of the starting material, (20R)-hydroxymethyl-4-methyl-4-aza5,7-pregnadien-3-one, and 46 mg of (20R)-hydroxymethyl-4-methyl-4-aza-5-alpha-7-pregnen-3-one as white needles (recrystallized from ethyl acetate), m.p. 196°–199° C.

EXAMPLE 7

4-methyl-4-aza-5-alpha-1,8(14)-androstadien-3-one-17β-N,N-diisopropylcarboxamide A solution of 4-methyl-4-aza-8 ([14]-androsten 3-one-17β-N,N-diisopropylcarboxamide (345 mg, 1 mmol) in 5 ml tetrahydrofuran at −70° C. is treated With a solution of lithium diisopropylamide in hexane-pentane (2 ml of 1.5M, 3 mmol) and allowed to warm to 0° C. This solution is then added to a solution of diphenyl disulfide (300 mg, 1.38 mmol) in 2 ml tetrahydrofuran and then allowed to stand for 2 hours at room temperature. The mixture is then partitioned between water and ethyl acetate. The organic layer is washed with dilute sodium hydroxide, water, dilute hydrochloric acid, water and brine and concentrated to a residue. The residue is dissolved in 10 ml methanol and treated at 0° C with an aqueous solution of sodium periodate (400 mg., 1.87 mmol, 2 ml water) for 2.5 hours. The mixture is diluted with water and precipitate is filtered and dried. The precipitate is dissolved in toluene, heated at reflux for 3 hours and then concentrated. Recrystallization from ethyl acetate affords 4-methyl-4-aza-5-alpha-1,8(14)-androstadien-3-one 17β-N,N-diisopropylcarboxamide.

EXAMPLE 8

4-Methyl-4-aza-5-alpha-8(14)-androsten-3-one-17β-ol

The title compound is prepared according to Example 1 by replacing testosterone for (20R-)-3-oxopregn 4ene-20-carboxaldehyde.

EXAMPLE 9

4-methyl-4-aza-5-alpha-8(14)-androsten-3,17-dione

A solution of 4-methyl-4-aza-8(14)-androsten-3one-17β-ol (301 mg, 1 mmol), prepared as in Example 8, in 10 ml acetone is treated with Jones Reagent until a red color persists. Excess reagent is quenched by addition of isopropanol. The solution is decanted from the thick, green chromium salts and the salts are then dissolved in water and extracted with dichloromethane. The combined organic layers are filtered through a bed of magnesium sulfate and concentrated to yield 4-methyl-4-aza-5-alpha8(14)-androsten-3,17-dione.

EXAMPLE 10

Ethyl 4-methyl-3-oxo-4-aza-5-alpha-pregn8(14)-17(20)-dien-21-oate

A solution of sodium ethoxide (2.8 g, 41 mmol) in 15 ml ethanol is added to a mixture of 4-methyl-4-aza-5alpha-8(14)-androsten-3,17-dione (4.0 g, 13.3 mmol), prepared as in Example 9, and methyl diethylphosphonoaetate (8.7 g, 41 mmol) and the resulting mixture heated at reflux for 4 hours. The mixture is cooled, concentrated, diluted with dilute aqueous acetic acid and extracted with ether. The combined ethereal extracts are washed with water, saturated aqueous sodium bicarbonate, brine, and concentrated to yield ethyl 4-methyl-3-oxo4-aza-5-alpha-pregn-8(14)-17(20)-dien-21-oate.

EXAMPLE 11

4-methyl-4-aza-5-alpha-8(14),16-androstadien3-one-17-trifluoromethyl sulfonate

A solution of 4-methyl-4-5-alpha-8(14) androsten-3,17-dione (3 g, 10 mmol), prepared as in Example 9, trifluoromethylsulfonic anhydride (3.8 g, 15 mmol), and 2,6-di-t-butyl-4-methyl-pyridine (2.6 g, 12.5 mmol) in 100 ml dichloromethane is stirred at room temperature for 4 hours. The resulting solution is concentrated. The residue is taken up in ethyl acetate-pentane, filtered, and washed with dilute HCl, aqueous sodium bicarbonate, brine, and then concentrated. Chromatography (silica, 7:3 ethyl acetate-hexane) yields 4-methyl-4-aza-5-alpha-8(14),16-androstadien-3-one17-trifluoromethyl sulfonate.

EXAMPLE 12

Methyl 4-methyl-4-aza-5-alpha-8(14),16-androstadien-3-one-17-carboxylate

A mixture of 4-methyl-4-aza-5-alpha-8(14),16-androstadien-3-one-17-trifluoromethylsulfonate (436 mg, 1 mmol), prepared as in Example 11, triethylamine (200 mg, 2 mmol), methanol (1.8 ml, 40 mmol), and bis(triphenylphosphine)palladium (II) acetate (22 mg, 0.03 mmol) in 4 ml dimethylformamide is stirred under an atmosphere of carbon monoxide for 4 hours. The mixture is then diluted with water and extracted with methylene chloride. The methylene chloride solution is concentrated and the residue chromatographed (silica, 5% methylene chloride) to yield methyl 4-methyl-4-aza-5-alpha-8(14),16-androstadien3-one-17-carboxylate.

EXAMPLE 13

4-Methyl-4-aza-5-alpha-8(14),16-androstadienone-17-carboxylic acid

4-Methyl-4-aza-5-alpha-8(14),16-androstadienone-17-carboxylic acid is prepared according to the procedure of Example 3 (iv) replacing hydroxyethyl 4-methyl-4-aza-8(14)-androsten-3-one-17β-carboxylate with methyl 4-methyl-4-aza-5-alpha-8(14)-androstadien-3-one17-carboxylate.

EXAMPLE 14

4-Methyl-4-aza-5-alpha-8(14),16-androstadien-3-one-17-N,N-diisopropylcarboxamide 4-methyl-4-aza-5-alpha-8(14),16-androstadien-3-one-17-N,N-diisopropylcarboxamide is prepared according to the procedure of Example 3 (vii) by replacing 4-methyl-4-aza-8(14)-androsten-3-one-17$\beta$-carboxylic acid with 4-methyl-4-aza-5-alpha-8(14),16-androstadien-3-one-17$\beta$-carboxylic acid.

EXAMPLE 15

N,N-Diisopropyl-4-methyl-3-oxo-4-aza-5-alpha-pregen-8(14),17(20)-dien-21-amide

N,N-Diisopropyl-4-methyl-3-oxo-4-aza-5-alpha -pregen-8(14),17(20)-dien-21-amide is prepared according to the procedure of Example 3 (vii) by replacing 4-methyl-4-aza-8(14)-androsten-3-one-17$\beta$-carboxylic acid with 4-methyl-3-oxo-4-aza-5-alpha-pregen-8(14),17(20)-dien-21-carboxylic acid.

EXAMPLE 16

2',3'alpha-Tetrahydrofuran-2'-spiro-17-(4-methyl-4-aza-8(14)-androsten-3-one

The process of Example 1 beginning with 2',3'alpha-tetrahydrofuran-2'-spiro-17-(4-androsten-3-one) yields 2'3'alpha-tetrahydrofuran-2'-spiro-17-(4-methyl-4aza-8(14)-androsten-3-one.

EXAMPLE 17

17$\beta$-Acetamido-4-methyl-4-aza-8(14)-androsten-3-one

The process of Example 1 beginning with - 17$\beta$-acetamido-4-androsten-3-one yields 17$\beta$-acetamido-4-methyl-4-aza-8(14)-androsten-3-one.

EXAMPLE 18

17-Carbomethoxy-4-methyl-4-aza-5alpha8(14)-androstene-3-one-17-ol

4-Methyl-4-aza-5-alpha-8(14)-androstene-3,17-dione (303 mg) is dissolved by gentle warming in 0.5 ml of freshly prepared acetone cyanohydrin. After two hours at room temperature the precipitated solid is collected to afford the cyanohydrins as a mixture of epimers at C-17. The mixture is dissolved in a solution of pyridine (1 ml) and acetic anhydride (1 ml) and allowed to stand at room temperature for 48 hours. Removal of the solvents under reduced pressure affords an oil which is dissolved in ether and washed with 1 n hydrochloric acid followed by aqueous sodium bicarbonate. The organic solution is dried and concentrated to afford the cyanohydrin acetates as a mixture of epimers at C-17.

The mixture of cyanohydrin acetates is dissolved in anhydrous methanol and cooled to 15 degrees. Dry hydrochloric acid is bubbled in and the mixture allowed to stand at room temperature for 2 hours. Solvent is then removed under reduced pressure. A mixture of tetrahydrofuran (2 ml) and water (w ml) is added followed by sodium hydroxide pellets (1 g) and the mixture is stirred for 2 hours at room temperature, then acidified and extracted with dichloromethane. The mixture of hydroxyacids which is obtained on concentration is dissolved in ether and treated with diazomethane to afford the hydroxy methyl esters. Chromatography on silica gel affords 17$\beta$-carbomethoxy-4-methyl-4-aza-5-alpha-(14) androstene-3-one-17-ol.

EXAMPLE 19

17$\beta$-(5)Ietrazololyl-4-methyl-4-aza-5-alpha8(14)-androstene-3-one

17-Carbomethoxy-4-methyl-4-aza-5-alpha-8(14) androstene-3-one (303 mg), prepared as in Example 18, in tetrahydrofuran (5 ml) at $-78°$ C. is treated slowly with Redal (0.5 mmol) and the solution maintained at $-78°$ C. for 2 hours then treated with aqueous ammonium chloride. The mixture is extracted with ether, the organic solution washed with brine, dried and concentrated to afford 17-carboxyaldehyde-4-methyl-4-aza-5-alpha-8(14)-androstene3-one.

This is then dissolved in pyridine (0.5 ml) and treated with hydroxylamine hydrochloride (80 mg) at room temperature overnight. The mixture is diluted with ether, and washed with water and brine then dried and evaporated to afford the oxime of 17-carboxaldehyde-4-methyl-4-aza5-alpha-8(14)-androstene-3-one.

This was dissolved in dichloromethane (2 ml) and treated with 1,1'-carbonyldiimidazole (165 mg). After 1 hour at room temperature the solution was diluted with dichloromethane and washed with water, then brine, then dried and concentrated to afford 17-carbonitrile-4-methyl4-aza-5-alpha-8(14)-androstene-3-one.

This was dissolved in dimethylforamide (2 ml) and treated with sodium azide (55 mg), lithium chloride (50 mg) and benzylamine hydrochloride (10 mg). The mixture was then heated at 110° C. for 24 hours. On cooling, the solution was diluted with water and in hydrochloric acid (1 ml) and the precipitated tetrazole filtered off and dried.

EXAMPLE 20

An oral dosage form for administering the presently invented compounds is produced by screening, mixing, and filling into hard gelatin capsules the ingredients in the proportions shown in Table V, below.

TABLE V

| Ingredients | Amounts |
| --- | --- |
| 4-Methyl-4-aza-5-alpha-8(14)-androsten-3-one-17$\beta$-N,N-diisopropylcarboxamide | 50 mg |
| magnesium stearate | 5 mg |
| lactose | 75 mg |

EXAMPLE 21

The sucrose, calcium sulfate dihydrate and 4-aza-5-alpha-8(14)-17-substituted-androsten-3-one shown in Table VI below, are mixed and granulated in the proportions shown with a 10% gelatin solution. The wet granules are screened, dried, mixed with the starch, talc and stearic acid, screened and compressed into a tablet.

TABLE VI

| Ingredients | Amounts |
| --- | --- |
| 4-Methyl-4-aza-5-alpha-8(14)-androsten-3-one-17$\beta$-N,N-diisopropylcarboxamide | 100 mg |
| calcium sulfate dihydrate | 150 mg |
| sucrose | 20 mg |
| starch | 10 mg |
| talc | 5 mg |
| stearic acid | 3 mg |

EXAMPLE 22

4-Methyl-3-oxo-4-aza-5-alpha-pregn-8(14),17(20)dien-21-carboxylic acid, 75 mg, is dispursed in 25 ml of normal saline to prepare an injectable preparation.

While the preferred embodiments of the invention are illustrated by the above, it is to be understood that the invention is not limited to the precise instructions herein disclosed and that the right to all modifications coming within the scope of the following claims is reserved.

What is claimed is:

1. A process for preparing a compound of the formula:

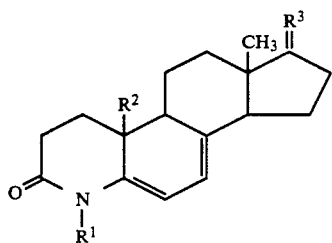

in which:

$R_1$ is H or $C_{1-4}$ alkyl;
$R_2$ is H or $C_{1-8}$ alkyl;
$R_3$ is
  (1) alpha-hydrogen, alpha-hydroxyl, or alpha-acetoxy and
  (a)

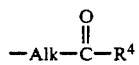

where Alk is absent of present as a straight or branched hydrocarbon chain of 1 to 12 carbons, and $R^4$ is
    (i) hydrogen,
    (ii) hydroxyl,
    (iii) $C_{1-8}$ alkyl,
    (iv) hydroxy $C_{1-8}$ alkyl,
    (v) $C_{1-8}$ alkoxy,
    (vi) $NR^5R^6$, where $R^5$ and $R^6$ are each independently selected from hydrogen, $C_{1-8}$ straight or branched chain alkyl, $C_{3-6}$ cycloalkyl, phenyl, or
    (vii) $OR^7$, where $R^7$ is hydrogen, alkali metal, $C_{1-18}$ straight or branched chain alkyl, benzyl, or
  (b) —Alk—$OR^8$, where Alk is always present and has the same meaning as above, and $R^8$ is
    (i) phenyl $C_{1-6}$ alkylcarbonyl,
    (ii) $C_{5-10}$ cycloalkylcarbonyl,
    (iii) benzoyl,
    (iv) $C_{1-8}$ alkoxycarbonyl,
    (v) amino, or $C_{1-8}$ alkyl substituted amino, carbonyl, or
    (vi) hydrogen, provided that Alk is a branched $C_3$-$C_8$ chain,
  (2) =CH—Alk—CO—$R^4$ or =CH—Alk—$OR^8$, where Alk is present or absent and has the same meaning as above, and $R^4$ and $R^8$ have the same meaning as above and $R^8$ also is hydrogen or $C_{1-20}$ alkylcarbonyl;
  (3)

where the dashed bond replaces the 17-alpha hydrogen,
  (4) alpha-hydrogen and $NHCOR^9$ where $R^9$ is $C_{1-12}$ alkyl or $NR^5R^6$ where $R^5$ and $R^6$ have the same meaning as above,
  (5) alpha-hydrogen and cyano,
  (6) alpha-hydrogen and tetrazolyl, or
  (7) keto, that comprises reacting with ammonia or a $C_{1-4}$ alkylamine a compound of the formula:

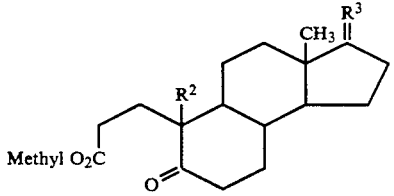

in which $R^2$ and $R^3$ are as defined above.

* * * * *